United States Patent
Yang (10) Patent No.: US 9,879,211 B2
(45) Date of Patent: Jan. 30, 2018

(54) LARGE HORIZONTAL DEVICE FOR CONTINUOUS METHANE FERMENTATION AND METHOD THEREOF

(71) Applicant: Beijing University of Technology, Beijing (CN)

(72) Inventor: Hong Yang, Beijing (CN)

(73) Assignee: Beijing University of Technology, Beijing (CN)

( * ) Notice: Subject to any disclaimer, the term of this patent is extended or adjusted under 35 U.S.C. 154(b) by 0 days.

(21) Appl. No.: 15/510,806

(22) PCT Filed: Jul. 21, 2015

(86) PCT No.: PCT/CN2015/084553
§ 371 (c)(1),
(2) Date: Mar. 13, 2017

(87) PCT Pub. No.: WO2016/041410
PCT Pub. Date: Mar. 24, 2016

(65) Prior Publication Data
US 2017/0253842 A1  Sep. 7, 2017

(30) Foreign Application Priority Data

Sep. 17, 2014 (CN) .......................... 2014 1 0476086

(51) Int. Cl.
*C12M 1/107* (2006.01)
*C12M 1/00* (2006.01)

(52) U.S. Cl.
CPC ............ *C12M 21/04* (2013.01); *C12M 27/18* (2013.01); *C12M 27/20* (2013.01); *C12M 29/00* (2013.01); *C12M 45/06* (2013.01); *C12M 45/20* (2013.01)

(58) Field of Classification Search
CPC ...... C12M 21/04; C12M 27/20; C12M 27/18; C12M 29/00; C12M 45/06; C12M 45/20;
(Continued)

(56) References Cited

U.S. PATENT DOCUMENTS 5,091,315 A * 2/1992 McCarty .................. C02F 3/28
210/320

FOREIGN PATENT DOCUMENTS

| CN | 200971358 Y | 11/2007 |
|---|---|---|
| CN | 101712923 A | 5/2010 |
| CN | 103881901 A | 6/2014 |

\* cited by examiner

*Primary Examiner* — Michael L Hobbs (57) ABSTRACT

A large-type horizontal device and a method for continuous methane fermentation. The whole distribution of a fermentation compartment uses a U-shape plane layout, which is a snap-back type and uses a material propeller. The material propeller has two axes and two blades and is constantly occluded with counter rotation. The irreversible propulsion of materials can be realized through counter rotation of two occluded blades. The propeller is set at the bottom of the main partition of the fermentation compartment. The propel ability of propeller can be changed through changing of rotation speed. Counter rotation of two occluded blades can realize material propeller without material reverting. The inlet and outlet entrances of the reactor in the disclosure are near to the ground and can be operated conveniently. The homogeneous output of materials and entire plug-flow can be realized at the same time without material mixing in the whole process.

3 Claims, 11 Drawing Sheets

(58) Field of Classification Search
CPC .... C05F 17/02; C05F 17/027; C05F 17/0247; C05F 17/0229; B09B 3/00
USPC .......................................... 435/290.1–290.4
See application file for complete search history.

LARGE HORIZONTAL DEVICE FOR CONTINUOUS METHANE FERMENTATION AND METHOD THEREOF

CROSS REFERENCE TO RELATED APPLICATION

This application is a national stage application of International application number PCT/CN2015/084553, filed Jul. 21, 2015, titled "Large horizontal device for continuous methane fermentation and method thereof," which claims the priority benefit of Chinese Patent Application No. 201410476086.5, filed on Sep. 17, 2014, which is hereby incorporated by reference in its entirety.

TECHNICAL FIELD

This disclosure belongs to the field of dry biogas fermentation, and more particularly to a large-type horizontal device and a method for continuous methane fermentation.

BACKGROUND

The problems exist all over the world that limits sustainable development such as shortage of resource, the mono structure of energy and environmental degradation, to build a resource-saving and environment-friendly society, strengthen production of clean energy combined with the development of environment protection technics and integrated application. Improving technical supporting and guiding capacity to sustainable development are an important component in technology development all over the world; some of the center technics are to utilize biomass resource and control the pollutant emission by biomass efficiently. To realize technology improvement and scale-up of new biomass energy industry, it must develop advanced and efficient biogas fermentation technologies according to the center fermentation technologies to develop large-scale biogas fermentation device.

Dry anaerobic fermentation usually indicates the content of dry matters in fermentation is about 20%-40%; materials are solid or semisolid, polluted liquids produced by fermentation, emit with little amount during treated process.

There are some problems existed in traditional biogas fermentation. 1) The continuous production of biogas fermentation cannot be reached, most of the large-scale device used batch-type. 2) The volume of dry fermentation compartment of large-scale device is too large, the content of dry matters in materials is high, and agitation is not homogeneous; 3) The fermentation time of biogas is too long, because of back mixing of materials (New, old), fermentation of materials output is not complete in outlet entrance; 4) Most of the large-scale fermentation device use reflux of fermentation broth for inoculation, it is difficult for a lot of materials to inoculate homogeneously. 5) Most of the biogas fermentation device use primary fermentation technics; so fermentation temperature is mesotherm fermentation, hydrolytic acidification and methanogenesis cannot be separated, reaction efficiency is low. The fundamental reasons for above-mentioned problems are: a lot of materials, agitation of high solid content materials and materials displacement is difficult.

The disclosure is based on this background mentioned above to develop a suitable large scale biogas fermentation type and specific device through the changing of agitation condition and driving forms of materials displacement.

SUMMARY

The disclosure relates to a large-type horizontal device and a method for continuous methane fermentation, which uses two-phase anaerobic technics. The process may be divided into hydrolytic acidification fermentation (mesotherm) and methanogenesis fermentation (high temperature).

The main content of disclosure is the design of materials inoculation, the way to propel large amount viscous semisolid materials, agitation approach for a lot of materials and the whole design for fermentation compartment. The disclosure can solve the conflict between viscous semisolid materials displacement without mixing and a large volume of single fermentation compartment in large-scale dry fermentation through an organic combination of the innovation of engineering design described above. The disclosure also provides a better technical approach for building large-scale or ultra-large-scale fermentation compartment. The whole fermentation system may include two parts: one is hydrolytic acidification part, and another is methane fermentation part. The form of two processes are same, but the volume of fermentation compartment and bacteria flora used in two processes is different (hydrolytic acidification: hydrolytic acidification flora; Methane fermentation: methane flora). The two forms will be described in one way to explain conveniently and avoid repetition.

Materials Inoculation Approach

The disclosure uses "ripe materials" which have been fermented completely mix with "raw materials" which have not been fermented to realize the form of bacteria inoculation of new materials. In design of disclosure, first whole distribution of fermentation compartment use U shape plane layout, which is snap-back type (in FIG. 1) to make feeding materials inoculation homogenizing compartment (1, 10) closer to fermentation ejection compartment (3, 12), it is benefit for transportation of "ripe materials" into feeding materials inoculation homogenizing compartment more convenient which guarantee the inoculation of "raw materials". Through materials inoculation device which is interconnected set between fermentation ejection compartment (3, 12) and feeding materials inoculation homogenizing compartment (1, 10) (Spiral transporting) to realize materials transportation. The material inoculator (4, 13) removed some "ripe materials" from fermentation ejection compartment and transported it into the feeding materials inoculation homogenizing compartment (1, 10). As for "ripe material" with bacteria which is fermented and "raw material" without being fermented, the process of material inoculation, material homogenizing and material entry the fermentation compartment is finished with the combined effect of methane fermentation material inoculator (4, 13), fermentation feed distributor (5, 14) and fermentation material propeller (7-1 to 7-6).

Materials Propel Approach

How to make the transportation of viscous semisolid materials largely and orderly has been a technical barrier for designing of large fermentation compartment. Using large material propeller self-designed in the disclosure can solve the problem efficiently.

Material propeller has two axes and two blades (30, in FIG. 10, 11), and it is constantly occluded with counter rotation. The irreversible propulsion of materials can be realized through counter rotation of two occluded blades. The propeller is set at the bottom of the main partition of fermentation compartment. Since the impeller blades which is applied long side design in rotation axis directions, a lot of materials can be propelled, propel ability of propeller can be changed through changing of rotation speed. These two occluded blades design can realize material propelling without reverse feeding.

Figure 3:
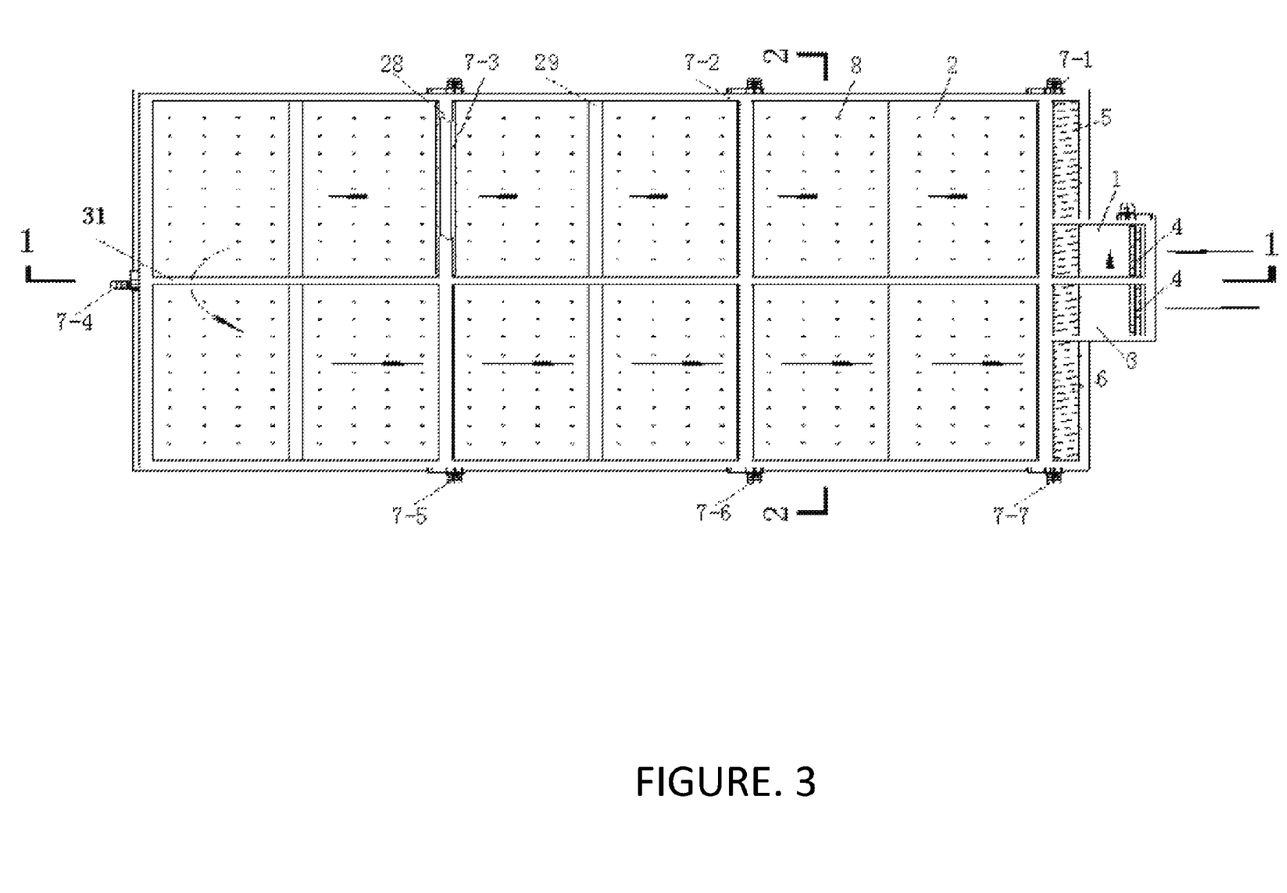
FIG. 3: planar diagram of methane fermentation compartment.
Figure 4:
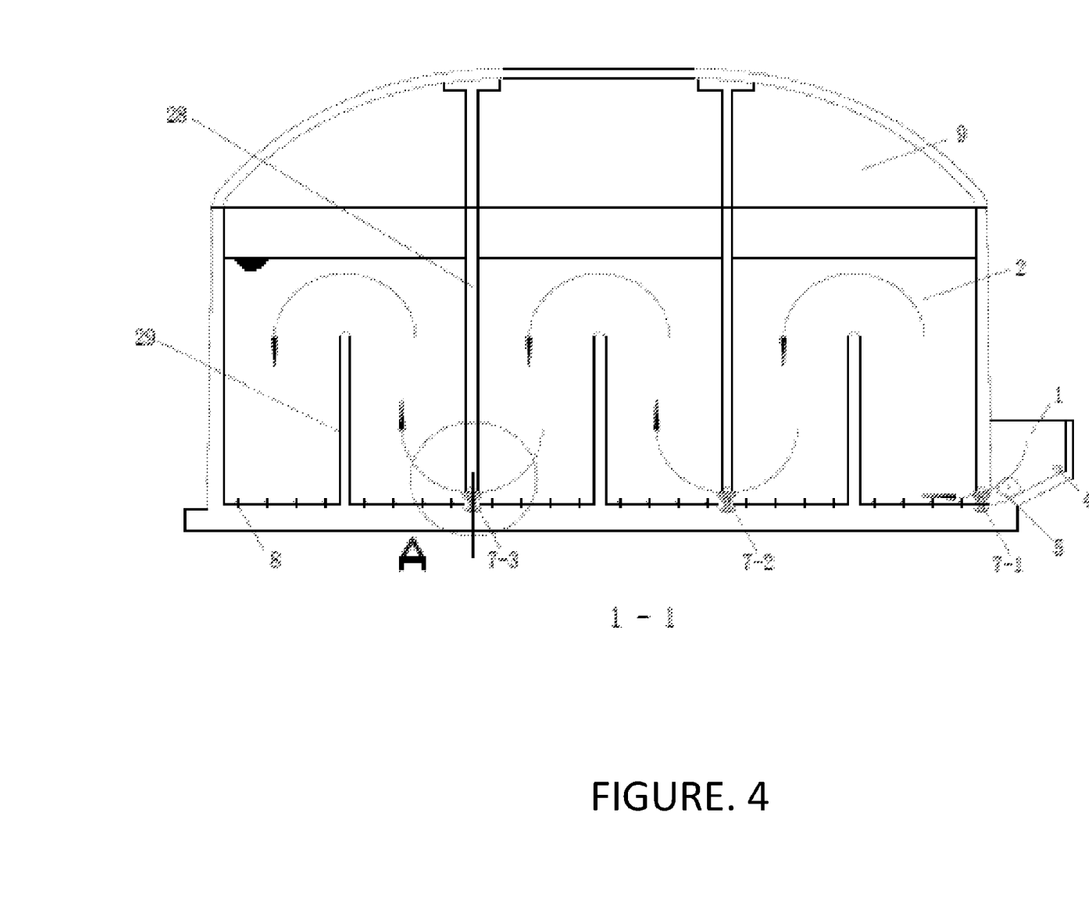
FIG. 4: the 1-1 cross-section diagram of fermentation compartment in FIG. 3.
Figure 5:
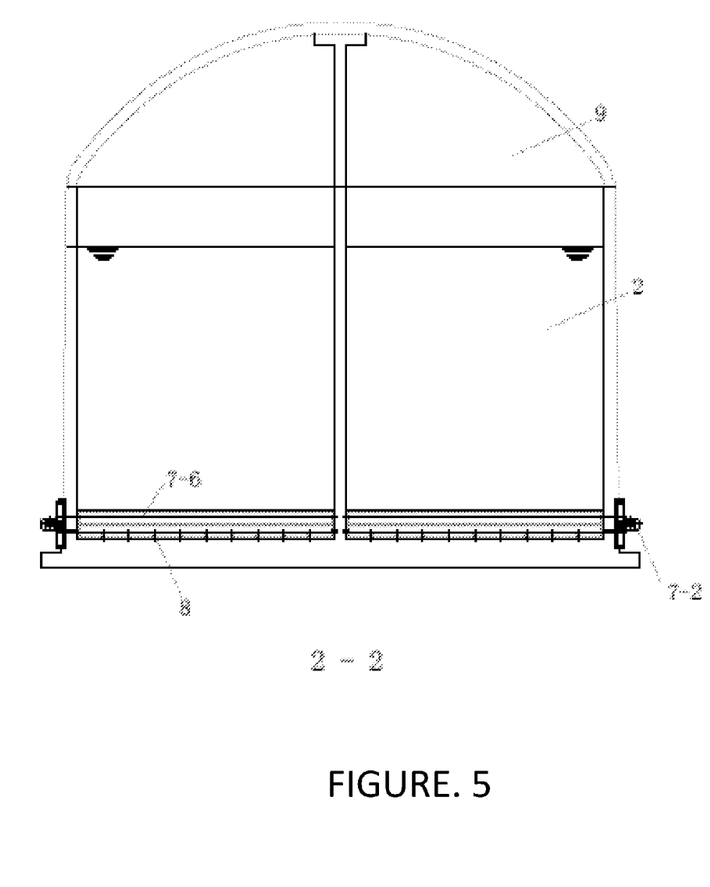
FIG. 5: the 2-2 cross-section diagram of fermentation compartment in FIG. 3.
Figure 6:
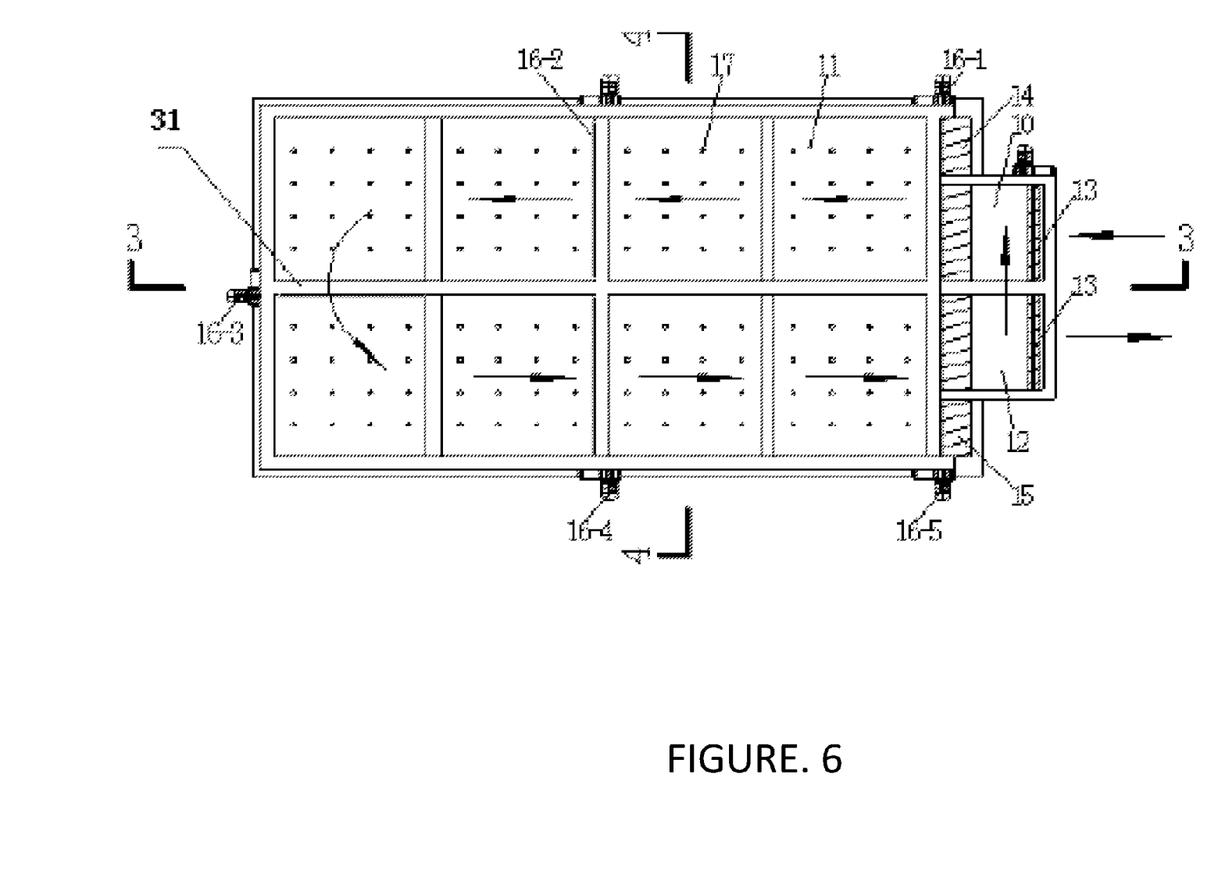
FIG. 6: planar diagram of hydrolysis compartment.
Figure 7:
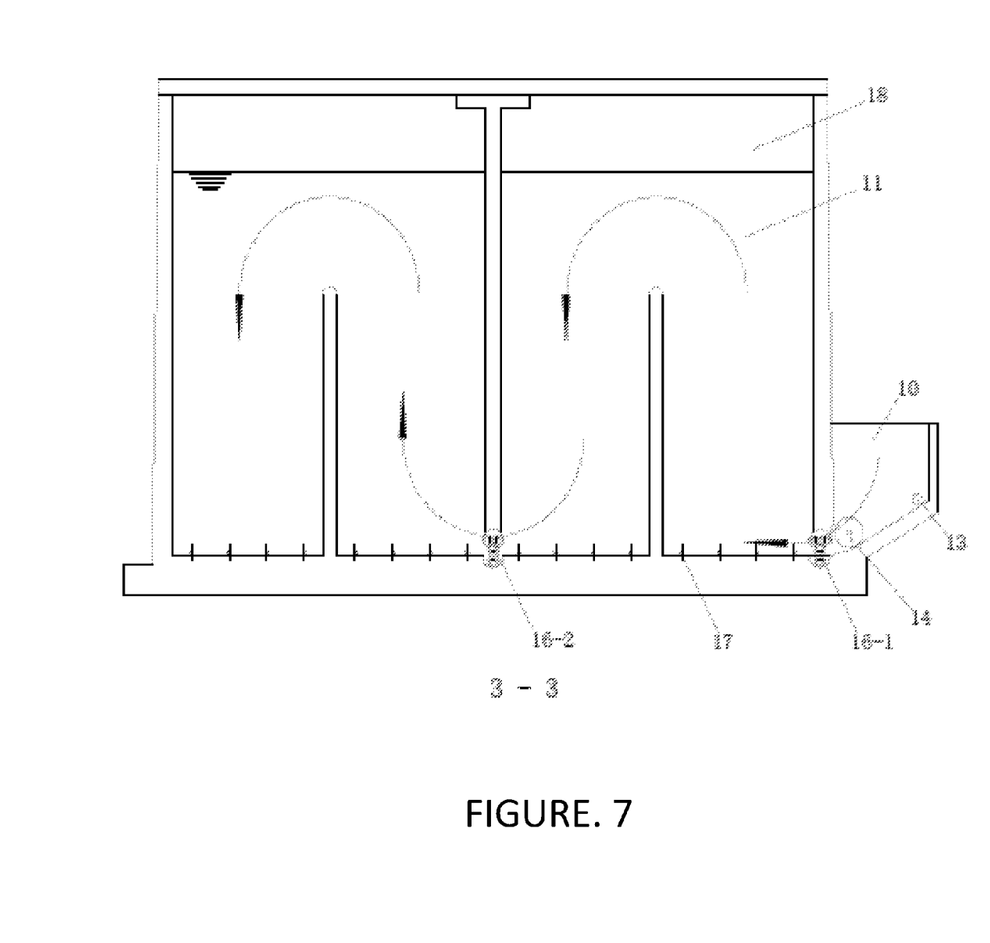
FIG. 7: 3-3 cross-section diagram of hydrolysis compartment in FIG. 6.
Figure 8:
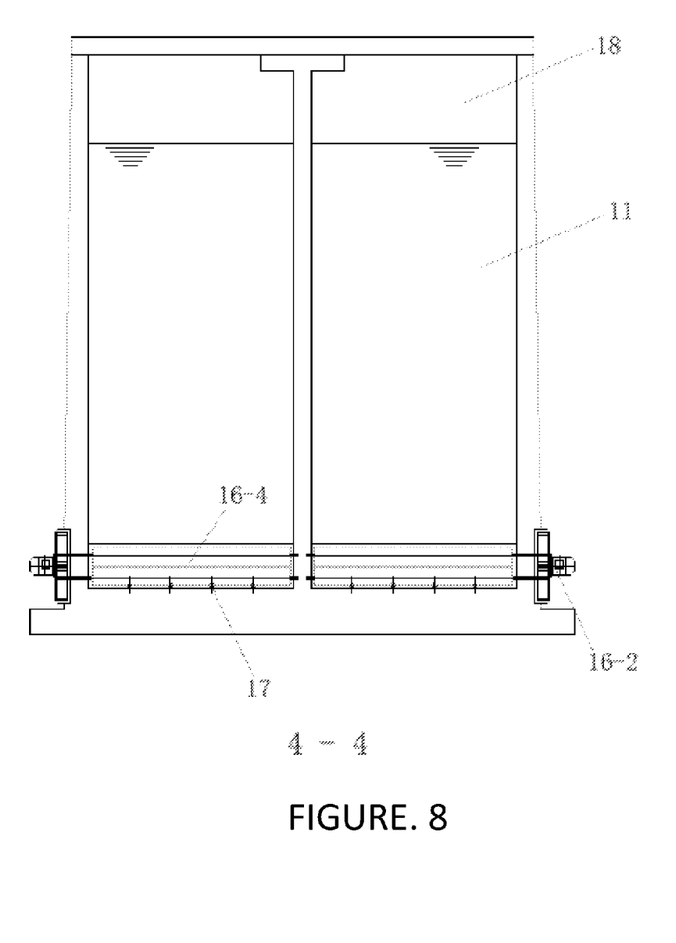
FIG. 8: 4-4 cross-section diagram of hydrolysis compartment in FIG. 6.
Figure 9:
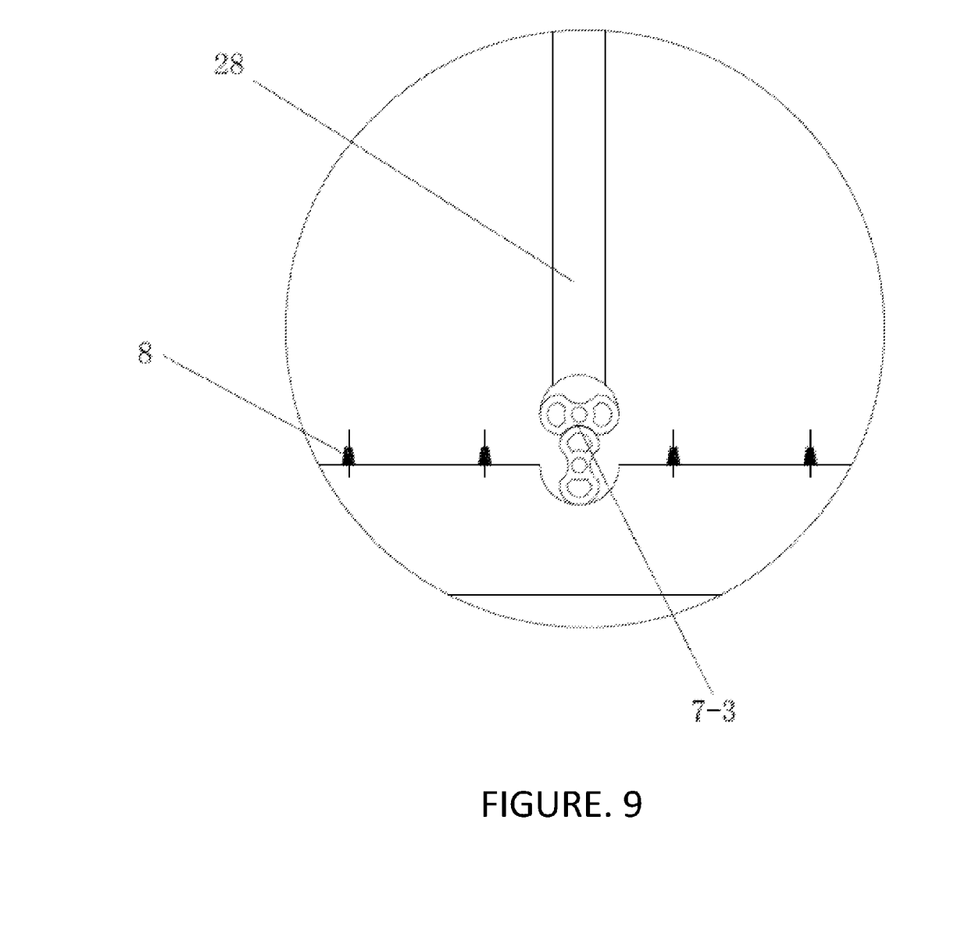
FIG. 9: enlarged diagram of section A in FIG. 4.

With the whole design of fermentation compartment, the disclosure set 5 material hydrolysis propellers (16-1 to 16-5) and 7 methane material propellers (7-1 to 1-7) under the hydrolysis fermentation compartment (11) and main partition (28, in FIG. 3) of methane fermentation compartment (2).

Materials Agitation

The disclosure uses air agitation, the material height of fermentation compartment is designed as 10 m, this height decreases more than a half compared with current fermentation compartment. The agitation process is more uniform since the lower material height of fermentation compartment, while, at the same time, it decreases outlet pressure largely of the air elevated pressure device. So, it can choose normally elevated pressure device to realize elevated pressure rather than the high-pressure device. In this way, the cost of the elevated device is decreased significantly.

To adapt and maintain an anaerobic environment for hydrolysis acidification and methane fermentation, the working approach of air agitation is provided as follow. Through elevated pressure device (22, 23 in FIG. 2), gas in collection part of fermentation compartment (18, 9 in FIG. 2) is absorbed and pressured. Biological waste gas with a large percentage of $CO_2$ generated by fermentation is collected in hydrolysis fermentation compartment. Methane fermentation gas which contains a large amount of methane is collected in methane fermentation compartment. The pressured gas is transported into gas distributor (14, 8) under fermentation compartment through gas distribution pipe; pressured gas is released from the gas distributor to do the agitation process of materials in fermentation compartment.

Fermentation Compartment

The key part of the disclosure is to design fermentation compartment. In process of solid and semisolid dry fermentation technics, volume of fermentation compartment is limited by material propel and agitation technics, in dry fermentation area, the largest volume of full-auto anaerobic fermentation compartment is about 5000 m³, and it limits large-scale biogas production significantly so that most of the current large-scale biogas production use the form of building many groups fermentation compartment to realize production.

The motion form of materials in fermentation compartment: with the help of material propeller (28) under the main partition on fermentation compartment, whole materials are propelled forward along the "flow" direction. Since material propeller is only set under the main partition (28), to protect material propel from short-circuit, there is parapet set in every unit grid to make the materials fully turn over in one grid, combined with material agitation, formed continuous forward, continuous agitation and continuous turnover in propelling process of whole material. Partial material homogenizing is realized while at the same time, there is no back mixing between materials with different fermentation level.

Feature of Fermentation Device

A large-type horizontal device and a method for continuous methane fermentation, wherein: hydrolysis feed compartment (24), hydrolysis heating feeder (25), hydrolysis feed heater (26), hydrolysis feeder (27), hydrolysis feed inoculation homogenizing compartment (10), hydrolysis inoculator (13), hydrolysis fermentation compartment (11), hydrolysis feed distributor (14), hydrolysis materials propeller (16-1 to 16-5), hydrolysis material ejection balancer (15), hydrolysis ejector (20), hydrolysis gas stirring distributor (17), hydrolysis gas circulation draught fan (22); methane fermentation feeder (21), methane fermentation and inoculation homogenizing compartment (1), methane fermentation material inoculator (4), methane fermentation compartment (2), methane fermentation feed distributor (5), methane fermentation material propeller (7-1 to 7-7), methane fermentation ejection balancer (6), methane fermentation ejection compartment (3), methane fermentation feed heater (19), methane fermentation stirring gas distributor (8), methane fermentation gas circulation draught fan (23), vertical main partition (31), parapet (29), and horizontal main partition (28);

Specifically, hydrolysis feed compartment (24) and hydrolysis feed heater (26) are connected through hydrolysis heating feeder (25), hydrolysis heating feeder (25) is in hydrolysis feed compartment (24) and run through hydrolysis feed heater (26), hydrolysis feed heater (26) connects hydrolysis feed inoculation homogenizing compartment (10) through hydrolysis feeder (27), hydrolysis feed inoculation homogenizing compartment (10) connects the inlet of hydrolysis fermentation compartment (11) through hydrolysis feed distributor (14), the outlet of hydrolysis fermentation compartment (11) connects hydrolysis ejection compartment (12) through hydrolysis material ejection balancer (15), hydrolysis feed inoculation homogenizing compartment (10) and hydrolysis ejection compartment (12) are connected through hydrolysis inoculator (13), meanwhile, hydrolysis ejection compartment (12) connects methane fermentation feed heater (19) through hydrolysis ejector (20), methane fermentation feed heater (19) connects methane fermentation feed inoculation homogenizing compartment (1) through methane fermentation feeder (21), methane fermentation feed inoculation homogenizing compartment (1) connects the inlet of methane fermentation compartment (2) through methane fermentation feed distributor (5), the outlet of methane fermentation compartment (2) connects methane fermentation ejection compartment (3) through methane fermentation ejection balancer (6), methane fermentation feed inoculation homogenizing compartment (1) and methane fermentation ejection compartment (3) are connected by methane fermentation material inoculator (4).

Methane fermentation compartment and hydrolysis fermentation compartment generally are reinforced concrete, for propelling materials in order, the vertical main partition is set in the middle of hydrolysis fermentation compartment, the vertical partition divides hydrolysis fermentation compartment into two parts, and set the route of materials in hydrolysis fermentation compartment is U-shape, and each part are divided into several grids by alternate horizontal main partitions and parapets, hydrolysis fermentation material propeller (16-1 to 16-5) is set under every horizontal main partition in each grid, in order to make the materials move forward up and down, besides, hydrolysis gas distributor for gas stirring (17) is installed at the bottom of the hydrolysis fermentation compartment, the top part of hydrolysis fermentation compartment is the assembly zone of hydrolysis gas (18), and the gas inside is ejected through hydrolysis gas distributor for gas stirring (17) after compression by hydrolysis gas circulation draught fan (22).

Methane fermentation compartment is same as hydrolysis fermentation compartment with two parts divided by vertical main partition and U-shaped material flowing route, each part are divided into several grids by alternate horizontal main partitions and parapets (29), methane fermentation material propeller (7-1 to 7-7) is set under horizontal main partition, forcing materials moving forward up and down in methane fermentation compartment, and methane fermentation stirring gas distributor (8) is set at the bottom of methane fermentation compartment, the top part of methane fermentation compartment is methane assemble zone (9), and the gas inside is ejected through methane fermentation gas distributor (23) after compression by methane fermentation gas circulation draught fan (8).

Figure 1:
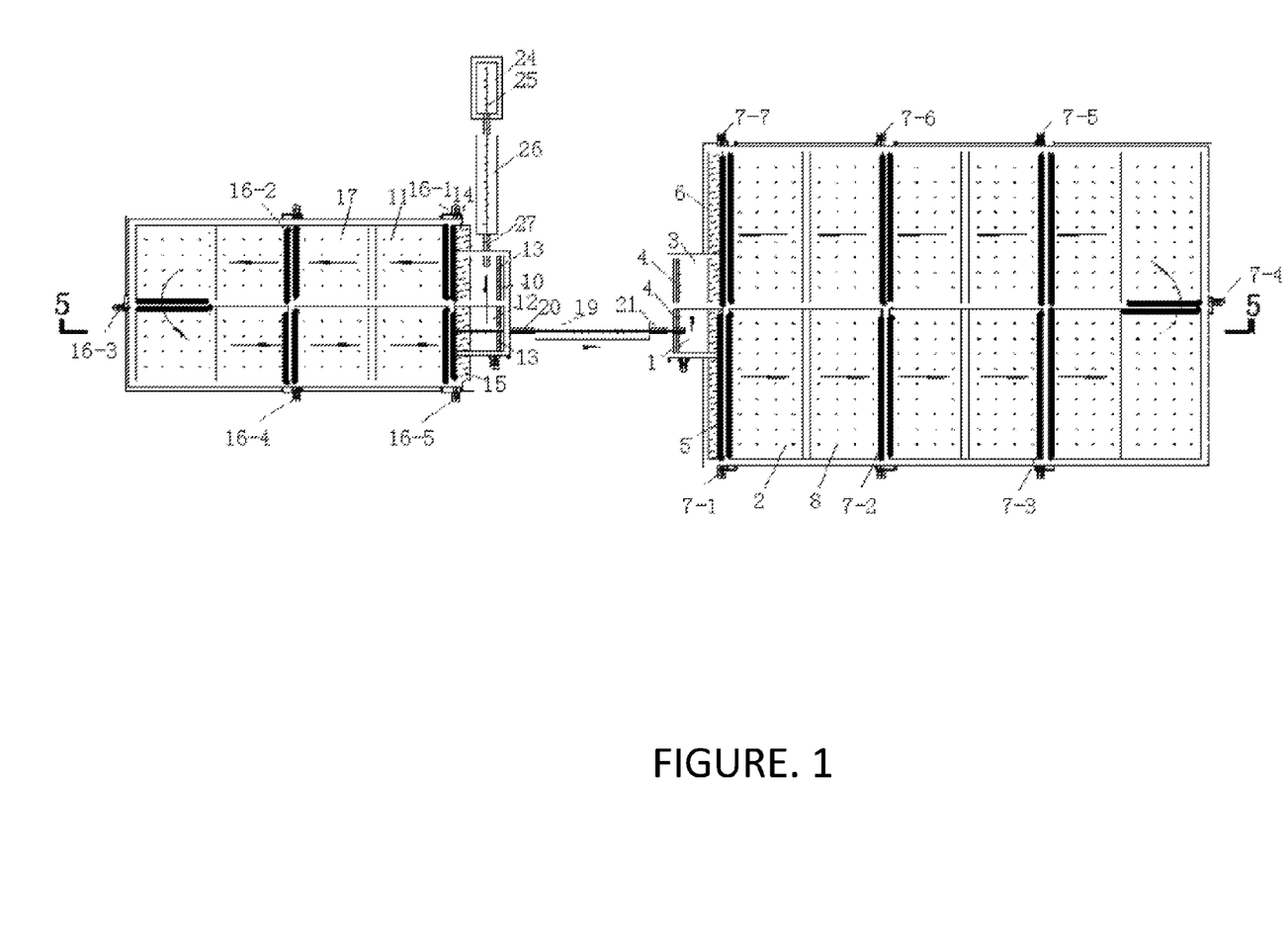
FIG. 1: the schematic diagram of large-type continuous methane fermentation device, as illustrated in FIG. 1, the two lines which are overstriking are material propellers.

To assure the connection of materials, there are material propellers under the reverse vertical main partitions at the end of both methane fermentation compartment and hydrolysis fermentation compartment (7-4, 16-3) in FIG. 1.

Figure 10:
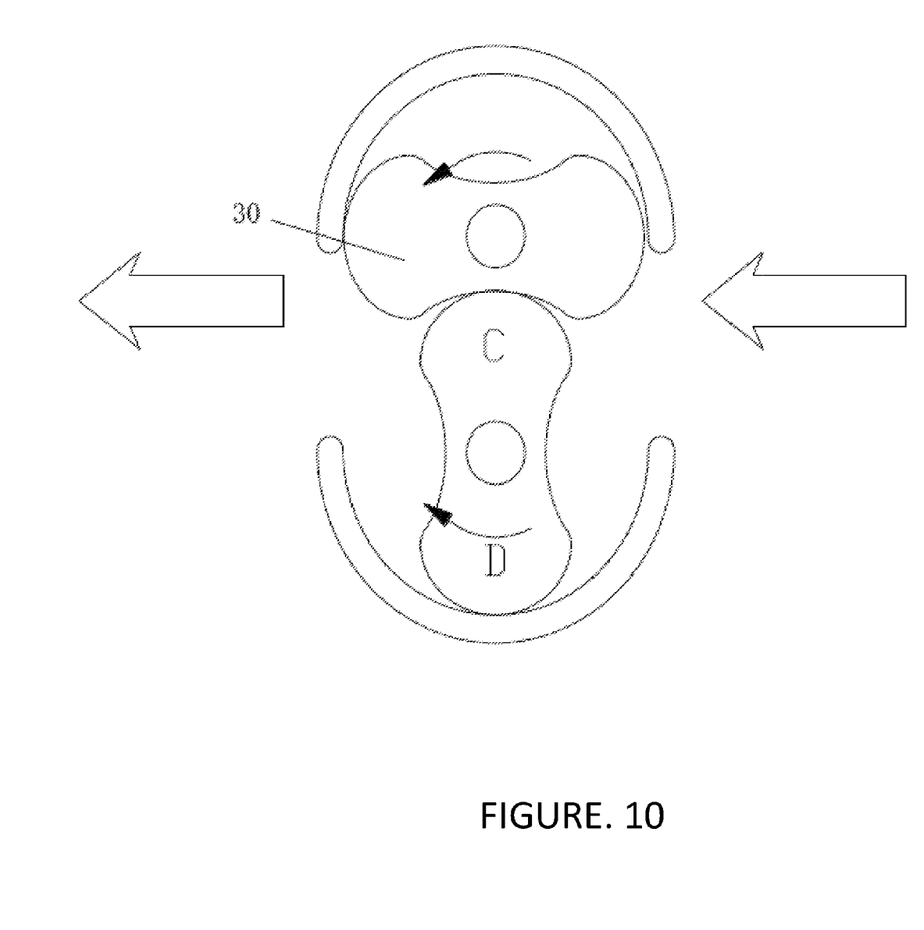
FIG. 10: structure diagram of material propeller.
Figure 11:
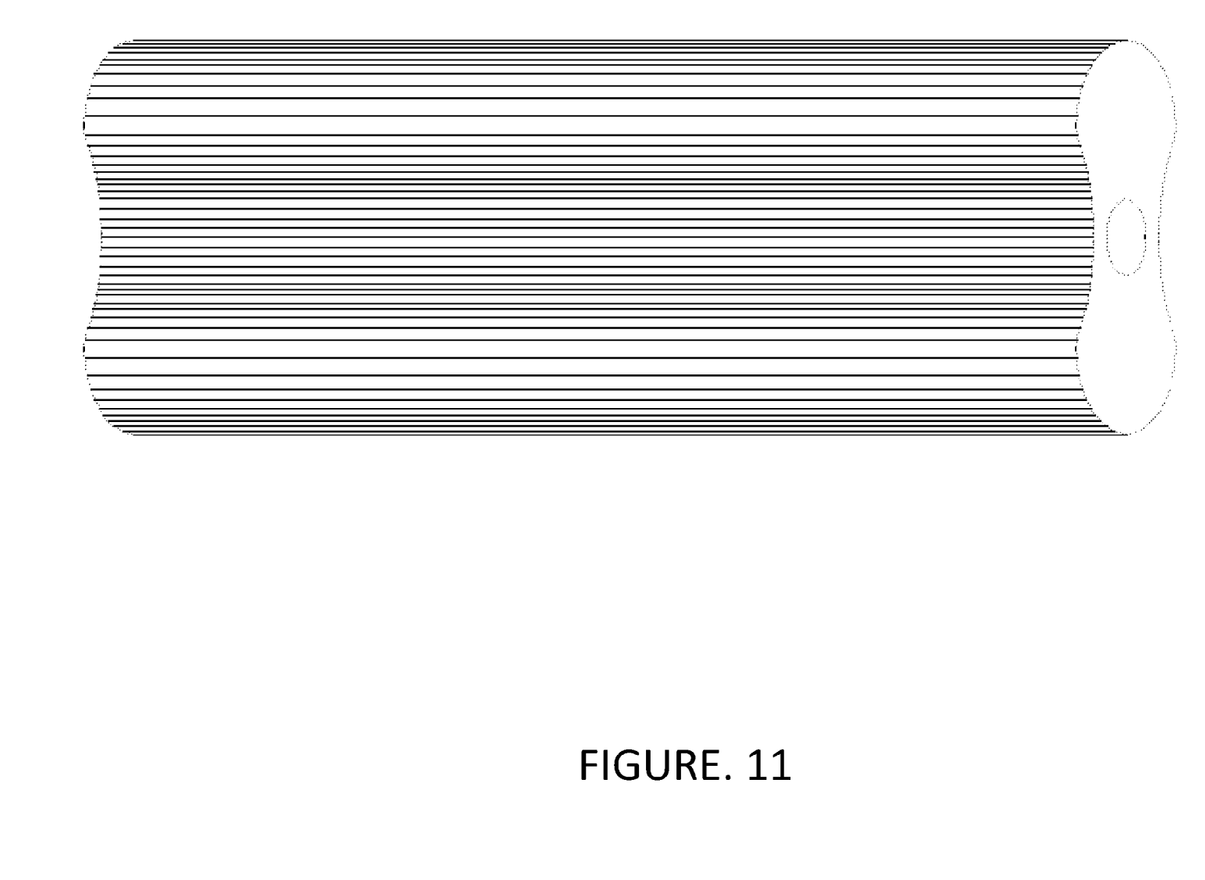
FIG. 11: structure diagram of long axis blade of the material propeller.

Every propeller includes: two long axis impellers, two propeller driving axis, and propeller shell, long axis impeller is a cylinder overall with impellers in axis direction, which means applying long side design in driving axis directions, and vertical cross-section is like a dumbbell with arcs at both ends and in the middle, each long axis impeller has a propeller driving axis, and two long axis impellers are parallel and synchronous rotate in reverse direction, one is clockwise while the other one is anticlockwise and two impeller blades are constantly occluded and seal in whole rotation process, outside each long axis impeller there is a propeller shell, and its internal surface is half arc, making the impeller is always tangent with corresponding half arc internal wall during the rotation, there are blocks set outside the propeller shells, dividing each side out of propeller into two parts, the viscous half-solid materials are transported from one side to the other side through the rotation of long axis impeller.

Material propeller is a horizontal rotation propeller set inner the compartment, and it is driven by driving device, material rotation propeller may include two counter rotating long axes propel blades immobilized on two axes, when the two blades is counter rotating, materials are propelled from the previous gird into next gird homogeneously, so, materials with bad flow condition will move forward homogeneously.

Material agitation in the disclosure, hydrolysis fermentation adopt hydrolysis waste gas is pressured by a fan and is released into the materials through hydrolysis gas agitation distributor set uniformly under fermentation compartment to realize uniform agitation of material. But since the whole material packing height of the disclosure is much lower than another dry fermentation device so that normal fan can be used in gas agitation elevated pressure device, lower the industry cost while at the same time improve system stability, the uniform level of agitation is also improved. Methane fermentation compartment uses the same approach with hydrolysis fermentation, but recycle gas is mixing methane generated by methane fermentation.

Material inoculation, dry fermentation generated less fermentation broth, this disclosure uses the fermented materials as inoculum, through the mixing with new materials to realize bacteria inoculation. The fermented materials go into feeding compartment with controlling through material inoculator (413) to realize new material inoculation; material homogenizing can be realized through the agitation of inoculator and gas distributor in homogeneous inoculation compartment.

Fermentation temperature and time, the temperature of hydrolysis fermentation is 33±2° C., fermentation stopping time is about 5-6 days. Methane fermentation temperature is 60-66° C., and methane fermentation stopping time is about 20 days.

Using the device above to do continuous fermentation process includes:

Put the fermenting materials in hydrolysis feed compartment (24) in proportion, then driven by hydrolysis heating feeder (25), the materials move into hydrolysis feed heater (26) and being heated, next, it is going to hydrolysis feed inoculation homogenizing compartment (10) driven by hydrolysis feeder (27), with combined effect of hydrolysis inoculator (13), hydrolysis feed distributor (14), and hydrolysis materials propeller (16-1), the materials are inoculated and homogenized and propelled in hydrolysis fermentation compartment (11), materials are stirred by the compressed gas flow from hydrolysis gas stirring distributor (17) in hydrolysis fermentation compartment, in the meantime, with the help of hydrolysis material propellers (16-2 to 16-4) set in fermentation compartment, materials move forward slowly along the flow direction, the whole hydrolysis fermentation lasts for 5 to 6 days, finally, the last hydrolysis material propeller (16-5) in hydrolysis fermentation compartment drive most materials into methane fermentation feed heater (19) through hydrolysis material ejection balancer (15) and hydrolysis ejector (20), a small amount of materials to hydrolysis feed inoculation homogenizing compartment (10) through hydrolysis inoculator (13) in order to finish the inoculation, that materials in methane fermentation feed heater (19) is being heated, and during the heating process, the hydrolysis acidize bacteria would be eliminated or inhibited at high temperature (60 to 65° C.).

Materials after hydrolysis, acidulation and heating would enter methane fermentation feed inoculation homogenizing compartment (1) through methane fermentation feeder (21), with the combined effect of methane fermentation material inoculator (4), methane fermentation feed distributor (5), methane fermentation material propeller (7-1), the materials are inoculated and homogenized, then it is propelled in methane fermentation compartment (2), with the help of methane fermentation material propellers (7-2 to 7-6) set in fermentation compartment, materials move forward slowly during the whole fermentation which lasts for 20 days, at last, the last methane fermentation material propeller (7-7) in methane fermentation compartment propels materials to methane fermentation ejection compartment (3) through methane fermentation ejection balancer (6), a little materials enters methane fermentation feed inoculation homogenizing compartment (1) through methane fermentation material inoculator (4) to finish the inoculation of methane bacteria, the other materials of outlet finishes the whole fermentation.

The disclosure can realize continuous fermentation.

During the continuous fermentation process, after passing hydrolysis feed heater (26), materials are heated up to 33±2° C., and the hydrolysis fermentation staying time is 5 to 6 days; after going through methane fermentation feed heater (19), the materials are heated up to 60 to 65° C., and the fermentation lasts for 20 days.

The volume adjustment of hydrolysis fermentation compartment and methane fermentation compartment is realized through adjusting the rotation speed of hydrolysis material propellers (16-1 to 16-5) and methane fermentation material propellers (7-1 to 7-7).

Advantage of the disclosure is: 1) continuous fermentation without material mixing is realized; 2) technics of the disclosure is simple, the need of mechanism unit is low, material inoculation uses mixed material approach, assure that the technics of the disclosure can be realized easily; 3) two anaerobic phase (first one, hydrolysis acidification with mesotherm, second one biogas fermentation with high temperature), maintains the reaction environment with each fermentation stage, high temperature inhibits the activity of hydrolysis acidification bacteria efficiently; 4) low packing height of fermentation materials (only half of current international technics); so it needs simple wind pressure device, and the agitation process is more uniform by using gas agitation; 5) material uniform output and plug flow is realized through whole propel approach of materials in fermentation compartment, it also realizes no material mixing during the whole reaction so that the fermentation is more complete.

To achieve the targets above, hydrolysis fermentation compartment and methane fermentation compartment use reinforced concert reaction pool, the material inlet and outlet entrance of the whole device are set to close to the ground, the operation is convenient and energy saving.

As illustrated in Figures above, 1 methane fermentation and inoculation homogenizing compartment; 2 methane fermentation compartment; 3 methane fermentation ejection compartment; 4 methane fermentation material inoculator; 5 methane fermentation feed distributor; 6 methane fermentation ejection balancer; 7 (7-1 to 7-7) methane fermentation material propeller; 8 methane fermentation stirring gas distributor; 9 assembly zone of methane gas; 10 hydrolysis feed inoculation and homogenizing compartment; 11 hydrolysis fermentation compartment; 12 hydrolysis ejection compartment; 13 hydrolysis inoculator; 14 hydrolysis feed distributor; 15 hydrolysis material ejection balancer; 16 (16-1 to 16-5) hydrolysis materials propeller; 17 hydrolysis gas stirring distributor; 18 assembly zone of hydrolysis gas; 19 methane fermentation feed heater; 20 hydrolysis ejector; 21 methane fermentation feeder; 22 hydrolysis gas circulation draught fan; 23 methane fermentation gas circulation draught fan; 24 hydrolysis feed compartment; 25 hydrolysis heating feeder; 26 hydrolysis feed heater; 27 hydrolysis feeder; 28 horizontal main partition; 29 parapet; 30 long axis propel blade; and 31 vertical main partition.

DETAILED DESCRIPTION OF THE PREFERRED EMBODIMENTS

The disclosure will be described in more detail below accompanying specific example with the preferred embodiments. But the disclosure is not only limited to this example.

The fermentation compartment technic design of the disclosure is no volume limitation, valid volume of methane compartment of the example is 5000 m³, height of material is 10 m (in planar graph 1, 2, cross-section diagram 1-1, 2-2, 3-3, 5-5), in practical application, whole compartment volume can be larger due to the material fermentation and agitation approach in the disclosure (In fact, if the design of fermentation compartment is cascade grid, another mechanical agitation approach can be used in single grid due to small volume of single grid material). The design of large compartment volume is realized by changing the number of grids and plane layout; so, this design has no technical barrier of the changing compartment volume.

Figure 2:
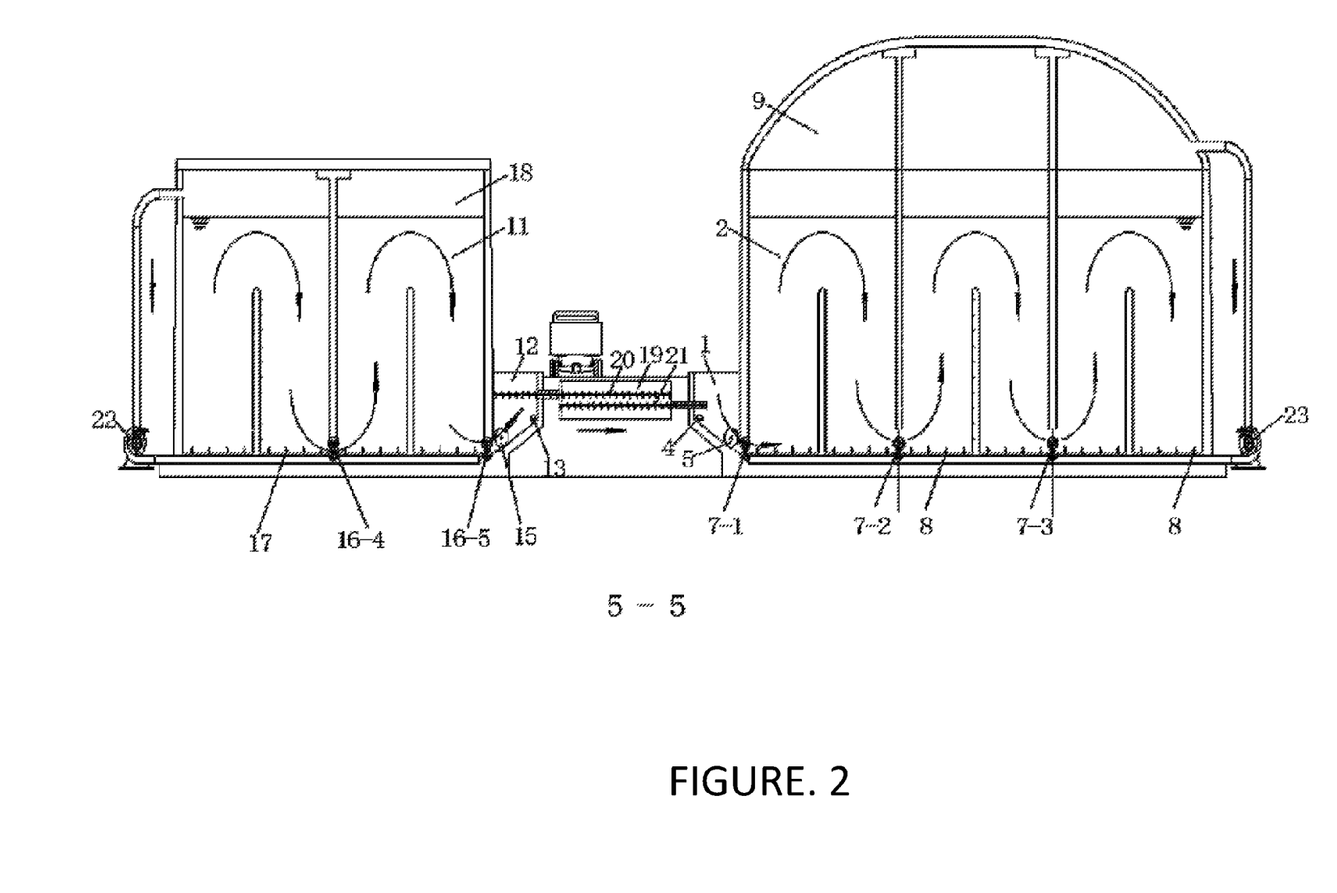
FIG. 2: the 5-5 cross-section diagram of FIG. 1.

The whole device of the example is shown in FIGS. 1 and 2; the partial structure is shown in FIG. 3 to FIG. 11.

The fermenting materials is put in hydrolysis feed compartment (24) in proportion, then driven by the hydrolysis heating feeder (25), the materials move into hydrolysis feed heater (26) and being heated, next, it is going to hydrolysis feed inoculation homogenizing compartment (10) driven by hydrolysis feeder (27), with the combined effect of hydrolysis inoculator (13), hydrolysis feed distributor (14), and hydrolysis materials propeller (16-1), the materials are inoculated and homogenized and propelled in hydrolysis fermentation compartment (11), materials are stirred by compressed gas flow from hydrolysis gas stirring distributor (17) in hydrolysis fermentation compartment, in the meantime, with the help of hydrolysis material propellers (16-2 to 16-4) set in fermentation compartment, materials move forward slowly along the flow direction, the whole hydrolysis fermentation lasts for 5 to 6 days, finally, last hydrolysis material propeller (16-5) in hydrolysis fermentation compartment drive most materials into methane fermentation feed heater (19) through hydrolysis material ejection balancer (15) and hydrolysis ejector (20), a small amount of materials to hydrolysis feed inoculation homogenizing compartment (10) through hydrolysis inoculator (13) in order to finish the inoculation, that materials in methane fermentation feed heater (19) is being heated, and during the heating process, the hydrolysis acidize bacteria would be eliminated or inhibited at high temperature (60 to 65° C.).

Materials after hydrolysis, acidulation, and heating will enter methane fermentation feed inoculation homogenizing compartment (1) through methane fermentation feeder (21), with the combined effect of methane fermentation material inoculator (4), methane fermentation feed distributor (5), methane fermentation material propeller (7-1), the materials are inoculated and homogenized, then it is propelled in methane fermentation compartment (2). Materials are agitated by the pressure drift produced by methane fermentation biogas stirring distributor (8) in methane fermentation compartment, at the same time, with the help of methane fermentation material propellers (7-2 to 7-6) set in fermentation compartment, materials move forward slowly during the whole fermentation which lasts for 20 days, at last, the last methane fermentation material propeller (7-7) in methane fermentation compartment propels materials to methane fermentation ejection compartment (3) through methane fermentation ejection balancer (6), a few materials enters methane fermentation feed inoculation homogenizing compartment (1) through methane fermentation material inoculator (4) to finish the new round of inoculation of methane bacteria, in this way to realize circulation-fermentation.

EXAMPLE 1

Compartment

It is made by reinforced concert structure; the valid volume of hydrolysis fermentation compartment is 1500 m³. The valid volume of methane fermentation compartment is 5000 m³.

Agitation

One of the key factors of dry fermentation of mixing material is agitation. The disclosure uses gas agitation, collecting the gas produced by fermentation, (hydrolysis waste gas of hydrolysis, methane fermentation mixing gas of methane), since the whole material packing height of the disclosure is much lower than another dry fermentation device so that normal fan can be used in gas agitation elevated pressure device, lower the industry cost while at the same time improve system stability, the uniform level of agitation is also improved.

Material Propeller

The disclosure uses a horizontal propeller with two blades under the condition of gas agitation. The material propeller is a horizontal propeller, and it is immobilized under the compartment driven by outer compartment. The horizontal propeller may include two long propel blades with counter rotation on two immobilized axes, during the counter rotation of two blades, the materials are transported from the previous gird into next gird homogeneously to make the materials with bad flow condition to flow forward homogeneously.

There are 7 material propellers set in methane fermentation compartment, 6 of these propellers have a 10 m axis, and 1 has a 4.2 m axis, there are 5 hydrolysis fermentation material propellers set in hydrolysis fermentation compartment, 4 of these propellers have a 5 m axis, and 1 has a 4.2 m axis.

Reaction Condition

The temperature of hydrolysis acidification is 33±2° C.; temperature of methane fermentation is 60-65° C.

Raw Material

70% dewater sludge with 80% moisture content generated by sewage plant mixed with 30% crushed kitchen waste.

Device Ability

Input: 250 m$^3$/d; hydrolysis fermentation stopping time: 6 days; methane fermentation stopping time: 20 days; gas produced by fermentation device: 25000 m$^3$/d.

What is claimed is:

1. A large horizontal device for continuous methane fermentation using fermenting materials, the device comprises:

a hydrolysis feed compartment, a hydrolysis heating feeder, a hydrolysis feed heater, a hydrolysis feeder, a hydrolysis feed inoculation and homogenizing compartment, a hydrolysis inoculator, a hydrolysis fermentation compartment, a hydrolysis feed distributor, a hydrolysis materials propeller, a hydrolysis material ejection balancer, a hydrolysis ejector, a hydrolysis gas stirring distributor, a hydrolysis gas circulation draught fan; a methane fermentation feeder, a methane fermentation and inoculation homogenizing compartment, a methane fermentation material inoculator, a methane fermentation compartment, a methane fermentation feed distributor, a methane fermentation material propeller, a methane fermentation ejection balancer, a methane fermentation ejection compartment, a methane fermentation feed heater, a methane fermentation stirring gas distributor, a methane fermentation gas circulation draught fan, a vertical main partition, a parapet, a horizontal main partition, wherein:

the hydrolysis feed compartment and the hydrolysis feed heater are connected through hydrolysis heating feeder, the hydrolysis heating feeder is in the hydrolysis feed compartment and runs through hydrolysis feed heater, the hydrolysis feed heater connects the hydrolysis feed inoculation homogenizing compartment through the hydrolysis feeder, the hydrolysis feed inoculation homogenizing compartment connects an inlet of hydrolysis fermentation compartment through the hydrolysis feed distributor, an outlet of hydrolysis fermentation compartment connects hydrolysis ejection compartment through a hydrolysis material ejection balancer, the hydrolysis feed inoculation homogenizing compartment and the hydrolysis ejection compartment are connected through the hydrolysis inoculator, the hydrolysis ejection compartment connects the methane fermentation feed heater through the hydrolysis ejector, the methane fermentation feed heater connects the methane fermentation feed inoculation homogenizing compartment through the methane fermentation feeder, the methane fermentation feed inoculation homogenizing compartment connects an inlet of methane fermentation compartment through the methane fermentation feed distributor, an outlet of methane fermentation compartment connects the methane fermentation ejection compartment through the methane fermentation ejection balancer, the methane fermentation feed inoculation homogenizing compartment and the methane fermentation ejection compartment are connected by the methane fermentation material inoculator;

the methane fermentation compartment and the hydrolysis fermentation compartment generally are reinforced concrete, the vertical main partition is set in the middle of the hydrolysis fermentation compartment for propelling materials in order, the vertical partition divides the hydrolysis fermentation compartment into two parts and sets route of materials in hydrolysis fermentation compartment to be U-shape, and each part are divided into several grids by alternate horizontal main partitions and parapets, hydrolysis fermentation material propeller is set under every horizontal main partition in each grid, in order to make the fermenting materials move forward up and down, besides, hydrolysis gas distributor for gas stirring is installed at the bottom of the hydrolysis fermentation compartment, the top part of hydrolysis fermentation compartment is an assembly zone of hydrolysis gas, and the gas inside is ejected through the hydrolysis gas distributor for gas stirring after compression the by hydrolysis gas circulation draught fan;

the methane fermentation compartment is the same as the hydrolysis fermentation compartment with two parts divided by a vertical main partition and a U-shaped material flowing route, each part are divided into several grids by alternate horizontal main partitions and parapets, a methane fermentation material propeller is set under the horizontal main partition in order to force the materials moving forward up and down in methane fermentation compartment, and a methane fermentation stirring gas distributor is set at the bottom of methane fermentation compartment, the top part of the methane fermentation compartment is an assembly zone of methane, and the gas inside is ejected through a methane fermentation gas distributor after compression by the methane fermentation gas circulation draught fan; and the material propellers are placed under reverse vertical main partitions at the end of both the methane fermentation compartment and the hydrolysis fermentation compartment to collect the fermenting materials, and wherein every propeller includes two long axis impellers, two propeller driving axis, and a propeller shell, each long axis impeller is a cylinder overall with impellers in an axis direction in order to apply a long side design in driving axis directions, and a vertical cross-section is like a dumbbell with arcs at both ends and in the middle, each long axis impeller has a propeller driving axis, and an axis of two long impellers is parallel and synchronous rotate in reverse direction, one is clockwise while the other one is anticlockwise and two impeller blades are constantly occluded and seal in the whole rotation process, outside each long axis impeller there is a propeller shell, and an internal surface is half arc, making the impeller be tangent with a corresponding half arc internal wall during the rotation, there are blocks set outside the propeller shells such asin order to divide each side out of the propeller into two parts, and the viscous half-solid materials are transported from one side to the other side through rotation of the long axis impeller.

2. The device of claim 1, wherein the fermenting materials in the hydrolysis feed compartment are put in proportion and then driven by the hydrolysis heating feeder, the fermenting materials are moved into a hydrolysis feed heater and are heated, the hydrolysis feed inoculation homogenizing compartment is driven by the hydrolysis feed feeder, the fermenting materials are inoculated, homogenized and propelled in the hydrolysis fermentation compartment using the hydrolysis inoculator, hydrolysis feed distributor, and hydrolysis materials propeller, the fermenting materials are stirred by the compressed gas flowing from a hydrolysis gas stirring distributor in the hydrolysis fermentation compartment, the materials are, in the meantime, moved forward slowly along the flow direction using the hydrolysis material propellers set in the fermentation compartment, the whole hydrolysis fermentation lasts for 5 to 6 days, the last hydrolysis material propeller in hydrolysis fermentation compartment drives most of the materials into the methane fermentation feed heater through the hydrolysis material ejection balancer and the hydrolysis ejector and one portion of the materials to the hydrolysis feed inoculation homogenizing compartment through the hydrolysis inoculator in order to finish the inoculation, the fermenting materials in the methane fermentation feed heater are heated, and the hydrolysis acidize bacteria are eliminated or inhibited at a high temperature (60 to 65° C.) during the heating process; and after hydrolysis, acidulation, and heating processes, the fermenting materials enter the methane fermentation feed inoculation homogenizing compartment through the methane fermentation feeder, the fermenting materials are re-inoculated and homogenized using the methane fermentation material inoculator, the methane fermentation feed distributor, and the methane fermentation material propeller and then are propelled in the methane fermentation compartment, the fermenting materials move forward during the whole fermentation, which lasts for 20 days using the methane fermentation material propellers set in fermentation compartment, the last methane fermentation material propeller in the methane fermentation compartment propels the fermenting materials to a methane fermentation ejection compartment through the methane fermentation ejection balancer, a portion of the fermenting materials enter the methane fermentation feed inoculation homogenizing compartment through the methane fermentation material inoculator to finish inoculation of methane bacteria, the rest portions of the fermenting materials of outlet finish the whole fermentation.

3. The device of claim 2, wherein: during the continuous fermentation process, after passing the hydrolysis feed heater, the fermenting materials are heated up to 33±2° C., and the hydrolysis fermentation staying time is 5 to 6 days; and after going through the methane fermentation feed heater, the fermenting materials are heated up to 60 to 65° C. for the fermentation lasts for 20 days.

* * * * *